(12) United States Patent
Schwemberger et al.

(10) Patent No.: US 7,886,953 B2
(45) Date of Patent: Feb. 15, 2011

(54) FIRED DEVICE LOCKOUT FOR A CURVED CUTTER STAPLER WITH A FREE MOVING TRIGGER

(75) Inventors: Richard F. Schwemberger, Cincinnati, OH (US); William D. Kelly, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 583 days.

(21) Appl. No.: 11/206,298

(22) Filed: Aug. 18, 2005

(65) Prior Publication Data
US 2007/0039995 A1  Feb. 22, 2007

(51) Int. Cl.
*A61B 17/072* (2006.01)
(52) U.S. Cl. .................. 227/178.1; 227/175.1; 227/19
(58) Field of Classification Search ............. 227/178.1, 227/175.2, 175.4, 180.1, 19
See application file for complete search history.

(56) References Cited

U.S. PATENT DOCUMENTS

| | | | | |
|---|---|---|---|---|
| 4,527,724 A | * | 7/1985 | Chow et al. ..................... 227/8 |
| 4,665,916 A | * | 5/1987 | Green ..................... 227/178.1 |
| 5,116,349 A | * | 5/1992 | Aranyi ..................... 227/181.1 |
| 5,413,267 A | | 5/1995 | Solyntjes et al. | |
| 5,462,215 A | * | 10/1995 | Viola et al. ............... 227/176.1 |
| 5,470,006 A | * | 11/1995 | Rodak ...................... 227/176.1 |
| 5,470,008 A | * | 11/1995 | Rodak ...................... 227/176.1 |
| 5,706,998 A | * | 1/1998 | Plyley et al. ............. 227/175.3 |
| 5,735,445 A | * | 4/1998 | Vidal et al. ............... 227/175.4 |
| 5,826,776 A | * | 10/1998 | Schulze et al. ........... 227/176.1 |
| 5,893,506 A | * | 4/1999 | Powell ..................... 227/175.3 |
| 6,805,273 B2 | * | 10/2004 | Bilotti et al. ............. 227/180.1 |
| 6,817,508 B1 | * | 11/2004 | Racenet et al. ........... 227/176.1 |
| 2005/0139632 A1 | * | 6/2005 | Schwemberger et al. . 227/175.2 |
| 2005/0139634 A1 | * | 6/2005 | Schwemberger et al. . 227/180.1 |

* cited by examiner

*Primary Examiner*—Rinaldi I. Rada
*Assistant Examiner*—Lindsay Low
(74) *Attorney, Agent, or Firm*—Welsh Flaxman & Gitler LLC

(57) ABSTRACT

A linear surgical stapler adapted for applying a plurality of surgical fasteners to body tissue includes an anvil structure and a cartridge housing containing a plurality of surgical fasteners and a knife. The cartridge housing and anvil structure are relatively movable between a first spaced apart position and a second position in close approximation with one another. A firing mechanism is associated with the cartridge housing for ejecting the surgical fasteners from the cartridge housing to be driven against the anvil structure. The firing mechanism includes a slide bar at its distal end adjacent the cartridge housing. A lockout mechanism interacts with the cartridge housing for selective activation and deactivation of the firing mechanism by disconnecting the distal end of the slide bar from a component housed within the cartridge housing.

20 Claims, 11 Drawing Sheets

FIRED DEVICE LOCKOUT FOR A CURVED CUTTER STAPLER WITH A FREE MOVING TRIGGER

BACKGROUND OF THE INVENTION

1. Field of the Invention

The present invention relates to surgical stapling and cutting instruments adapted for use in the diagnosis and therapy of pathologies treated by stapled resection. More particularly, the invention relates to a lockout mechanism for utilization in conjunction with surgical stapling and cutting instruments.

2. Description of the Prior Art

Surgical stapling and cutting instruments are commonly utilized in the diagnosis and treatment of pathologies treated by stapled resection. Surgical stapling and cutting instruments provide a mechanism to extend the transluminal exploitation of mechanical suturing devices introduced via the anal canal, mouth, stomach and service accesses. Although surgical stapling and cutting instruments are most commonly utilized with rectal pathologies, surgical stapling and cutting instruments may be used in a variety of environments.

Over time, surgical stapling and cutting instruments have been developed. These instruments generally include a support frame, an anvil attached to the support frame and a cartridge housing carrying a plurality of staples. The instruments also include a driver within the cartridge housing which pushes all of the staples out simultaneously into the anvil to form the staples into a generally B-shape, suturing tissue together. In addition, these instruments include approximation mechanisms that allow for the cartridge housing and anvil to move relative to each other to accept tissue therebetween. Finally, the instruments include a firing mechanism for moving the driver forward to form the staples against the anvil.

In addition to the basic components of the stapling and cutting instruments, these products need a lockout mechanism permitting activation and/or deactivation of the approximation means such that the cartridge module may be utilized as a clamp when needed during an emergency. However, the lockout mechanism is designed such that the firing mechanism only works for a cartridge module that has not been previously used.

Current surgical stapling instruments include a firing bar lockout that is activated by the driver. When a new cartridge module is loaded into the instrument, the location of the driver, as it relates to the cartridge module in the instrument, interferes with the lockout arm in a way so as to let the instrument fire staples. After the instrument fires staples, the location of the driver moves distally in a way that it no longer interferes with the lockout arm. The lockout arm moves to a position that now interferes with the firing bar, but prevents the firing bar from moving distally. However, prior art lockout mechanisms do not provide a clear indication that the instrument has been previously fired. As such, prior lockout mechanisms may be simply confused with an instrument that has been jammed.

In addition, prior lockout systems require the device to survive high stress if the user should try to defeat the lockout mechanism. As will be discussed below in greater detail, the present lockout mechanism disengages the firing mechanism altogether removing any force transmission that would require the device to survive high loads.

As such, a need exists for an improved lockout mechanism that provides a clear indication that the lockout mechanism has been activated and overcomes the other shortcomings of prior art lockout mechanisms. The present invention provides such a lockout mechanism.

SUMMARY OF THE INVENTION

It is, therefore, an object of the present invention to provide a surgical stapler adapted for applying a plurality of surgical fasteners to body tissue. The surgical stapler includes an anvil structure and a cartridge housing containing a plurality of surgical fasteners and a knife. The cartridge housing and anvil structure are relatively movable between a first spaced apart position and a second position in close approximation with one another. A firing mechanism is associated with the cartridge housing for ejecting the surgical fasteners from the cartridge housing to be driven against the anvil structure. The firing mechanism includes a slide bar at its distal end adjacent the cartridge housing. A lockout mechanism interacts with the cartridge housing for selective activation and deactivation. The lockout mechanism includes a lock tab that interferes with the slide bar of the firing mechanism moving the slide bar such that tabs on the slide bar move out of alignment with tabs on the knife during firing of the linear surgical stapler to prevent subsequent firing of the linear surgical stapler.

It is also an object of the present invention to provide a surgical stapler wherein the lock tab rotationally moves the slide bar.

It is another object of the present invention to provide a surgical stapler wherein during firing of the linear surgical stapler the firing mechanism moves the lock tab distally to a neutral position in the cartridge module.

It is a further object of the present invention to provide a surgical stapler wherein after the lock tab is moved distally the firing mechanism is retracted and a knife driver and the lock tab remain in the distal position in the cartridge module.

It is also another object of the present invention to provide a surgical stapler wherein retraction of the firing mechanism causes the knife and slide bar to be moved proximally away from the lock tab, and the slide bar rotates into its disconnect position.

It is yet another object of the present invention to provide a surgical stapler wherein the slide bar is spring biased.

It is a further object of the present invention to provide a surgical stapler wherein the lock tab is integrally formed with a cartridge housing of the cartridge module.

It is still a further object of the present invention to provide a surgical stapler wherein prior to actuation of the firing mechanism the slide bar includes distally extending prongs aligned with the knife and knife driver for subsequent contact therewith.

It is also an object of the present invention to provide a surgical stapler wherein prior to actuation of the firing mechanism the lock tab engages the slide bar to ensure that the prongs are properly aligned with knife tabs extending proximally from the proximal end of the knife.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
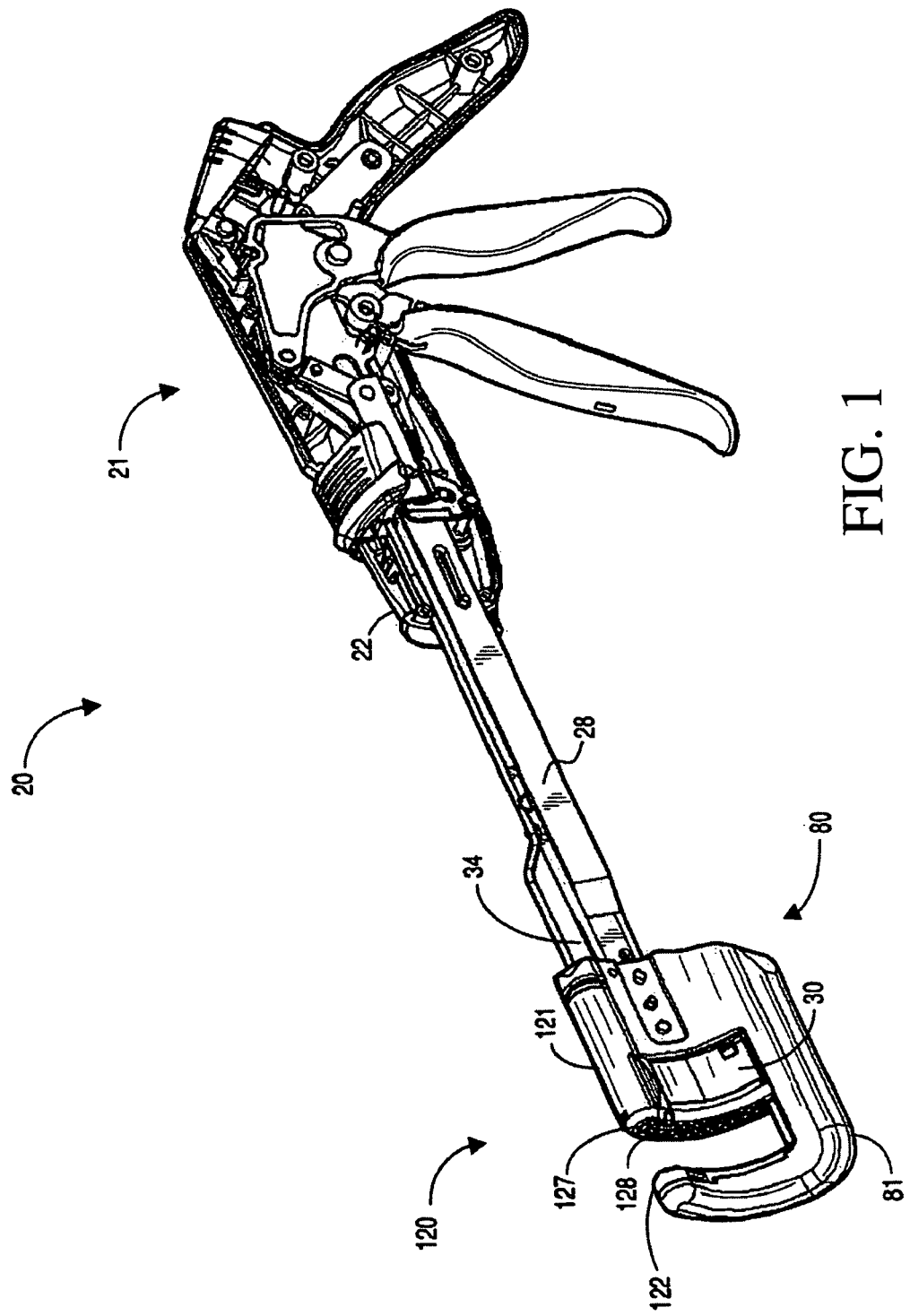
FIG. 1 is a perspective view of the linear surgical stapler in accordance with the present invention.
Figure 2:
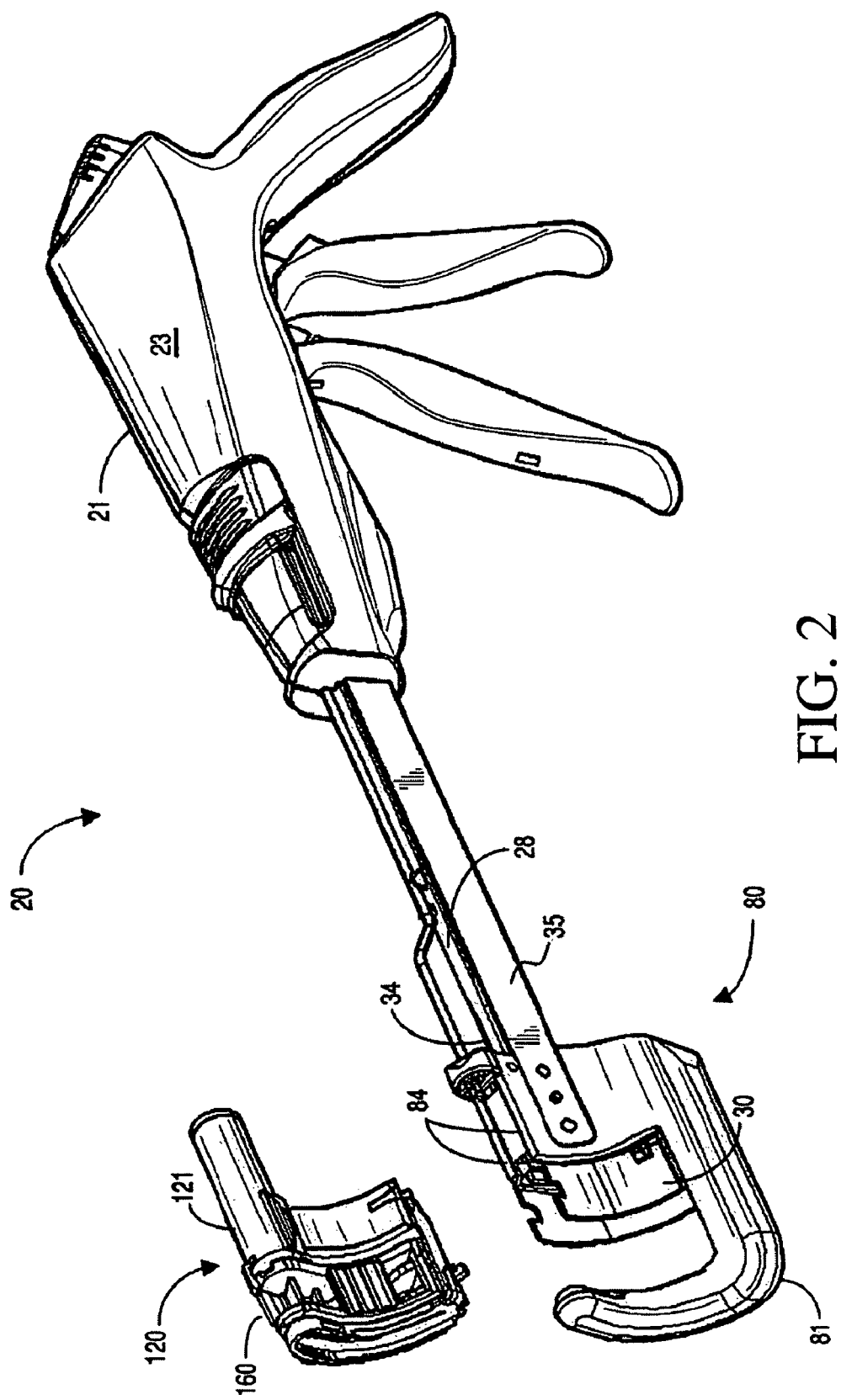
FIG. 2 is perspective view of the linear surgical stapler with the cartridge module removed.
Figure 3:
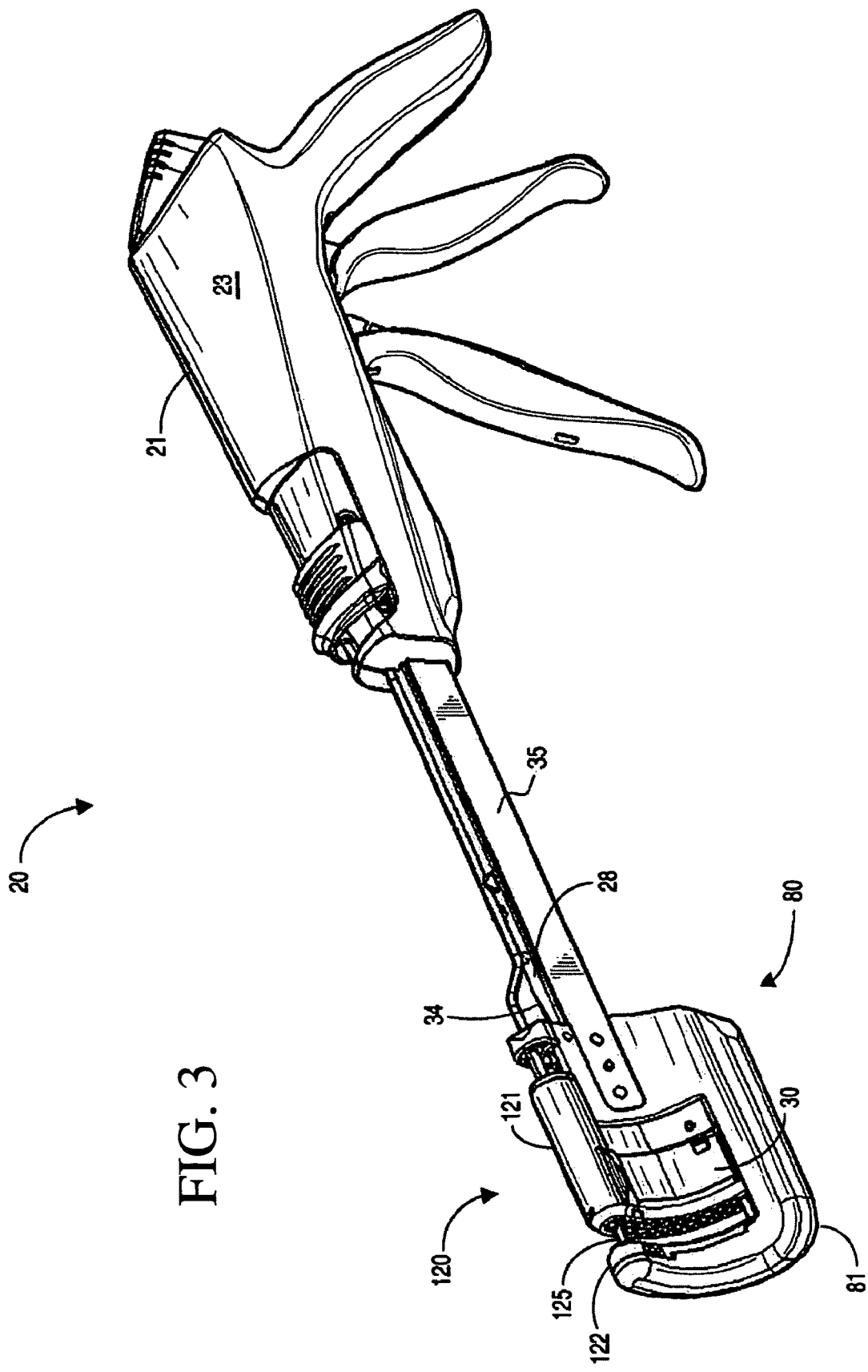
FIG. 3 is a perspective view of the linear surgical stapler with the cartridge housing moved to an intermediate position.
Figure 4:
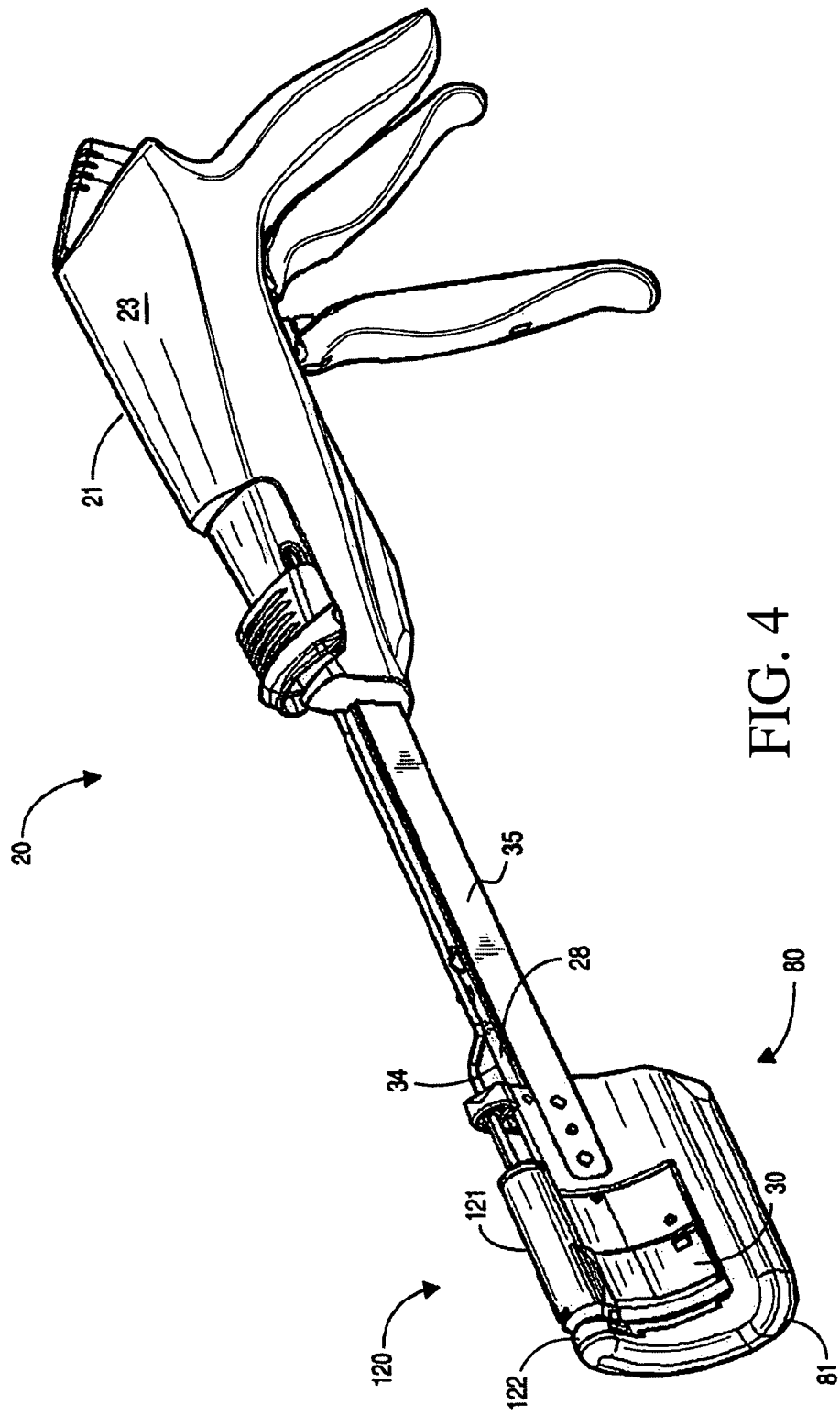
FIG. 4 is a perspective view of the linear surgical stapler with the cartridge housing moved to a closed position.
Figure 5:
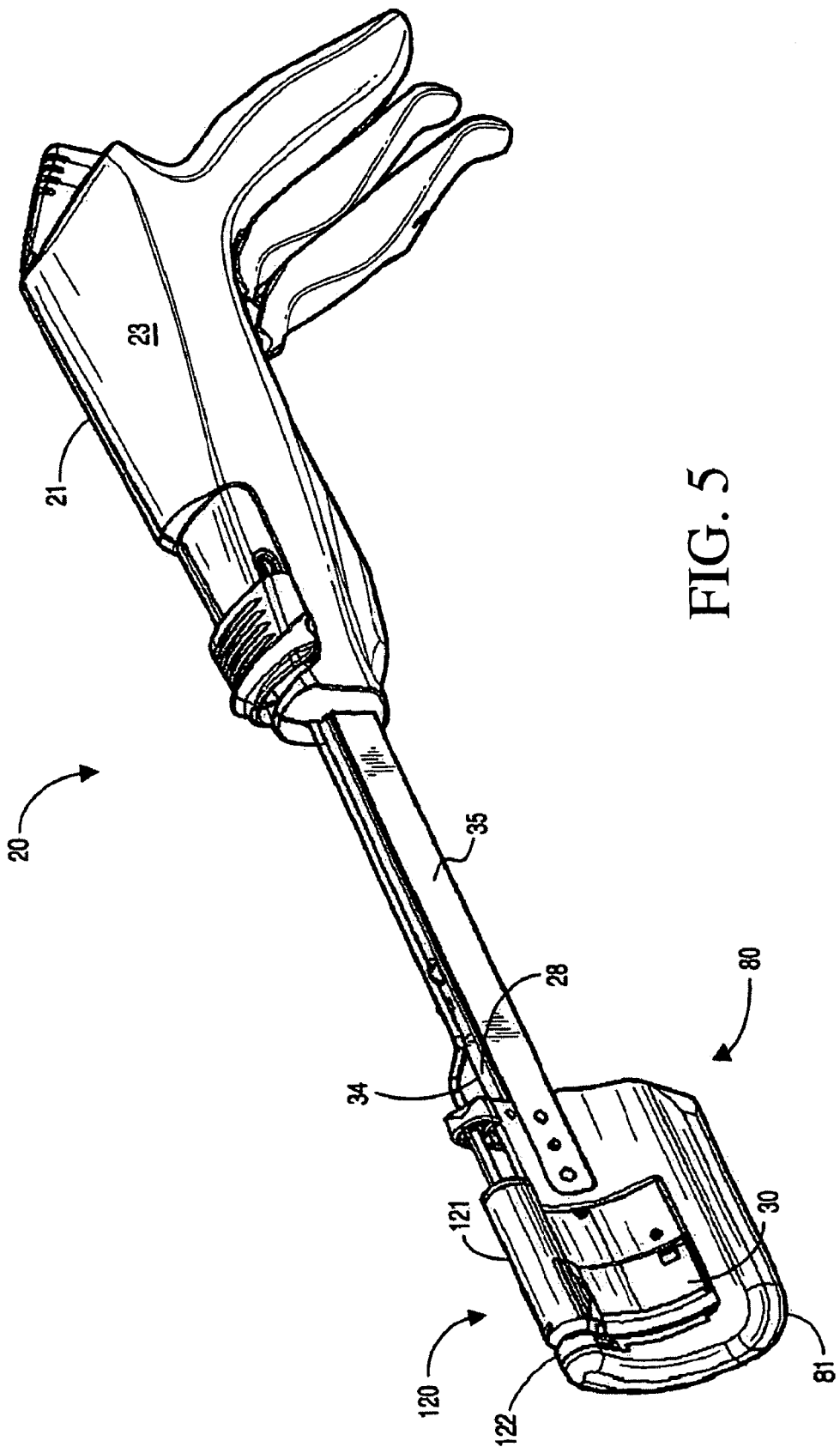
FIG. 5 is a perspective view of the linear surgical stapler with the firing trigger in a firing position.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, a surgical instrument 20 adapted for applying a plurality of surgical fasteners to body tissue is disclosed. The surgical instrument 20 includes an anvil 122 and a cartridge housing 121 containing a plurality of surgical fasteners. The cartridge housing 121 and anvil 122 are relatively movable between a first spaced apart position and a second position in close approximation with one another. A firing mechanism is associated with the cartridge housing 121 for ejecting the surgical fasteners from the cartridge housing 121 to be driven against the anvil 122. A lockout mechanism 180 interacts with the cartridge housing 121 for selective activation and deactivation of the closing mechanism. The lockout mechanism 180 includes a lock tab 182 that interferes with a slide bar 184 of the firing mechanism moving the slide bar 184 rotationally such that tabs 186 on the slide bar 184 move out of alignment with tabs 188 on the knife 126 during firing of the linear surgical stapler to prevent subsequent firing of the linear surgical stapler.

Referring to FIG. 1 in combination with FIGS. 2 to 5, there is shown a surgical stapling and cutting instrument, in particular, a linear surgical stapler 20 which is designed to staple and cut tissue. The linear surgical stapler 20 has a handle 21 at a first proximal end and an end effector 80 at an opposite distal end. The end effector 80 is curved in accordance with a preferred embodiment of the present invention. Right and left hand structural plates (often called "handle plates") 34, 35, respectively, connect the handle 21 to the end effector 80 of the instrument (the left hand handle plate is not shown in FIG. 1). The handle 21 has a right hand shroud 22 coupled to a left hand shroud (the left hand shroud is not shown in FIG. 1). The handle 21 also has a body portion 23 to grip and maneuver the linear surgical stapler 20 (see FIGS. 2 to 5).

The end effector 80 is a surgical fastening assembly that includes a cartridge module 120 and a C-shaped supporting structure 81 having side walls 84. The term C-shaped is used throughout the specification to describe the concave nature of the supporting structure 81 and the cartridge module 120. The C-shaped construction facilitates enhanced functionality and the use of the term C-shaped in the present specification should be construed to include a variety of concave shapes which would similarly enhance the functionality of surgical stapling and cutting instruments. Although a C-shaped construction is contemplated in accordance with a preferred embodiment of the present invention, those skilled in the art will appreciate the supporting structure may take various shapes without departing from the spirit of the present invention. The distal end 30 of a closure member 28 is disposed to receive the cartridge module 120. The end effector 80 also includes a safety lockout mechanism 180 (best seen in FIGS. 6 to 8) for preventing the firing of a previously fired cartridge module 120. The cartridge module 120 contains a cartridge housing 121 coupled to an anvil 122. The cartridge module 120 also includes a retaining pin 125, a knife 126, a removable retainer 160, a tissue contacting surface 127 which displays a plurality of staple-containing slots 128 in staggered formation in one or more rows (that is, staple lines) on either side of the knife 126. Staples (not shown) are fired from the cartridge housing 121 against staple-forming surface 129 of the anvil 122 that faces the tissue-contacting surface 127 of the cartridge housing 121.

As will become apparent based upon the following disclosure, the present linear surgical stapler 20 is designed as a multiple firing device with a replaceable cartridge module 120. However, it should be understood that many of the underlying concepts of the present invention may be equally applied in single firing devices without departing from the spirit of the present invention. With this in mind, operation of components other than the lockout mechanism are disclosed in commonly owned U.S. patent Ser. No. 11/014,910, entitled "CURVED CUTTER STAPLER SHAPED FOR MALE PELVIS", filed Dec. 20, 2004, which is incorporated herein by reference.

Figure 6:
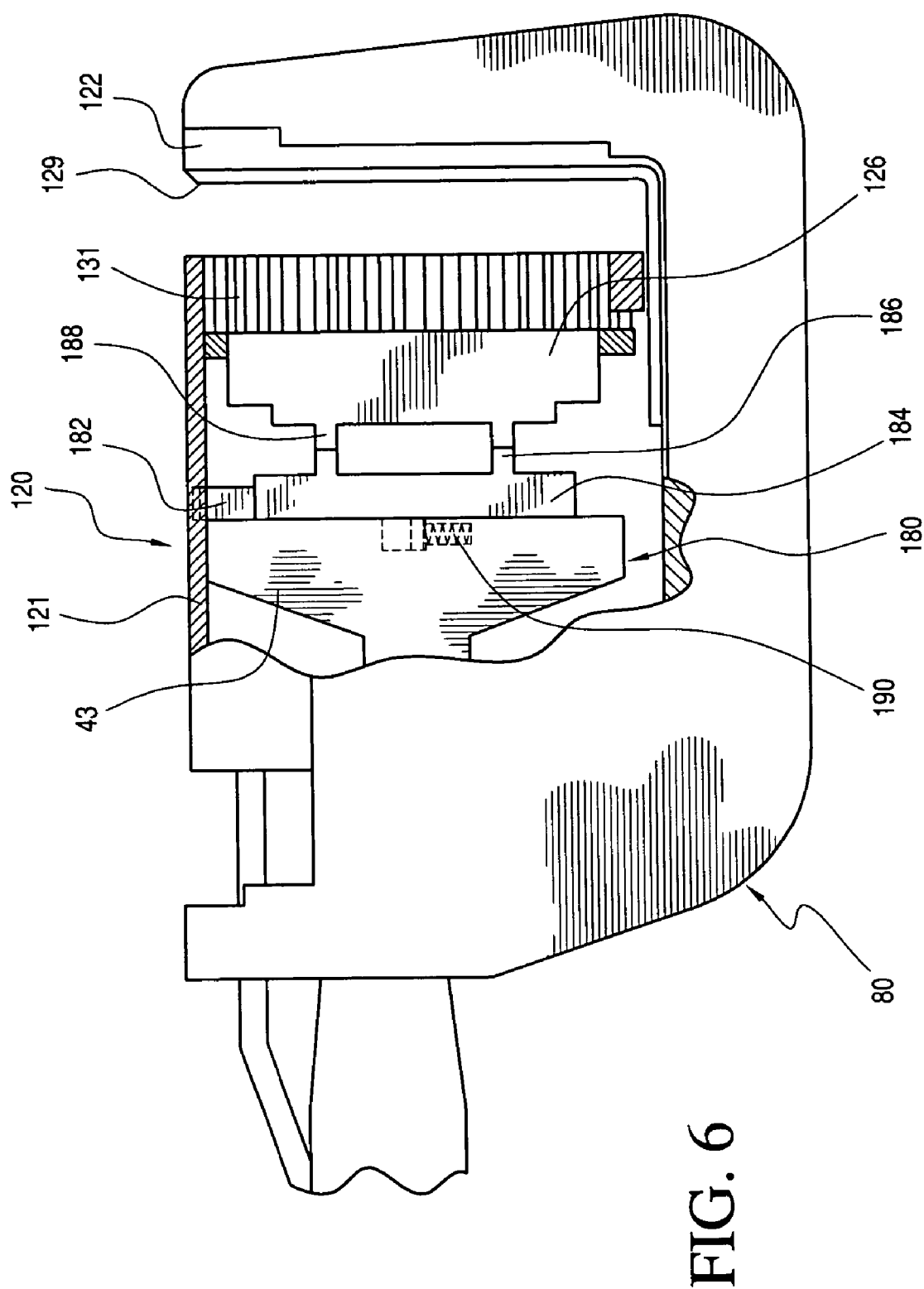
FIG. 6 through 8 show the various steps involved in the actuation of the present linear surgical stapler.

Referring to FIGS. 6 though 8 (cut away view into cartridge and support structure), the components of the fired device lockout mechanism 180 will now be described. In accordance with a preferred embodiment of the present invention, the cartridge module 120 is provided with a lock tab 182 that interferes with a slide bar 184 positioned at the distal end of the firing bar 43, moving the slide bar 184 rotationally so that tabs 186 on the slide bar 184 are positioned in line with tabs 188 on the knife 126 prior to firing.

When the firing transmission assembly is moved distally, the firing bar 43 moves the driver 131 and the knife 126 toward the tissue, thus stapling and cutting the predetermined tissue area. During firing, the firing bar 43 moves the lock tab 182 distally to a neutral position in the cartridge module 120. After the firing transmission assembly is retracted, the driver 131 and the lock tab 182 remain in the distal position in the cartridge module 120. The slide bar 184 then rotates into its disconnect position by a spring 190 because the lock tab 182 no longer forces it into its firing position.

It is contemplated the knife 126 will be moved proximally by either employing a spring loading mechanism (not shown) which will act to move the knife 126 rearwardly after firing or selectively locking hooks incorporated into the mating tabs of the slide bar and knife. It is contemplated the locking hooks would be similar to those used in linking the knife to the firing bar as disclosed in U.S. patent application Ser. No. 11/014,895, entitled "KNIFE RETRACTION ARM FOR A CURVED CUTTER STAPLER", which is incorporated herein by reference. It is further contemplated knife retraction could be accomplished by making the timing between slide bar and lock tab such that the tabs on the slide bar can hook into the knife (or vice versa) such that the rotation of the slide bar causes the disengagement of the retraction hooks between the knife and slide bar only after the knife has been retracted enough to prevent the knife from being exposed outside the cartridge.

The firing bar 43 is free to move distally thereafter as it will not engage or actuate either the driver 131 or knife 126. More particularly, the tabs 186 of the slide bar 184 will not move with the firing bar 43 because the tabs 186 of the slide bar 184 rotate into a disconnect position. The driver 131 remains in the forward proximal position.

Figure 7:
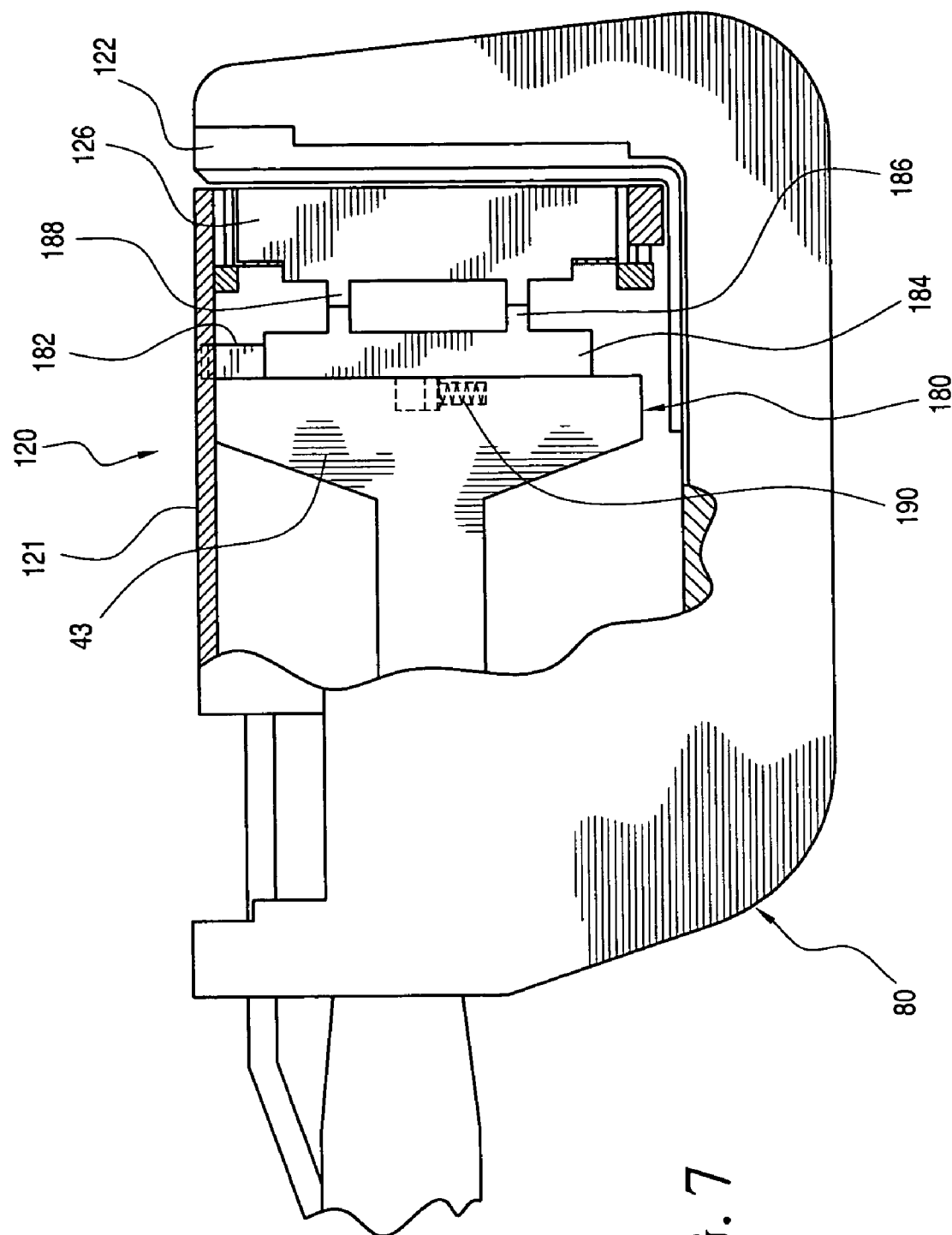
Figure 8:
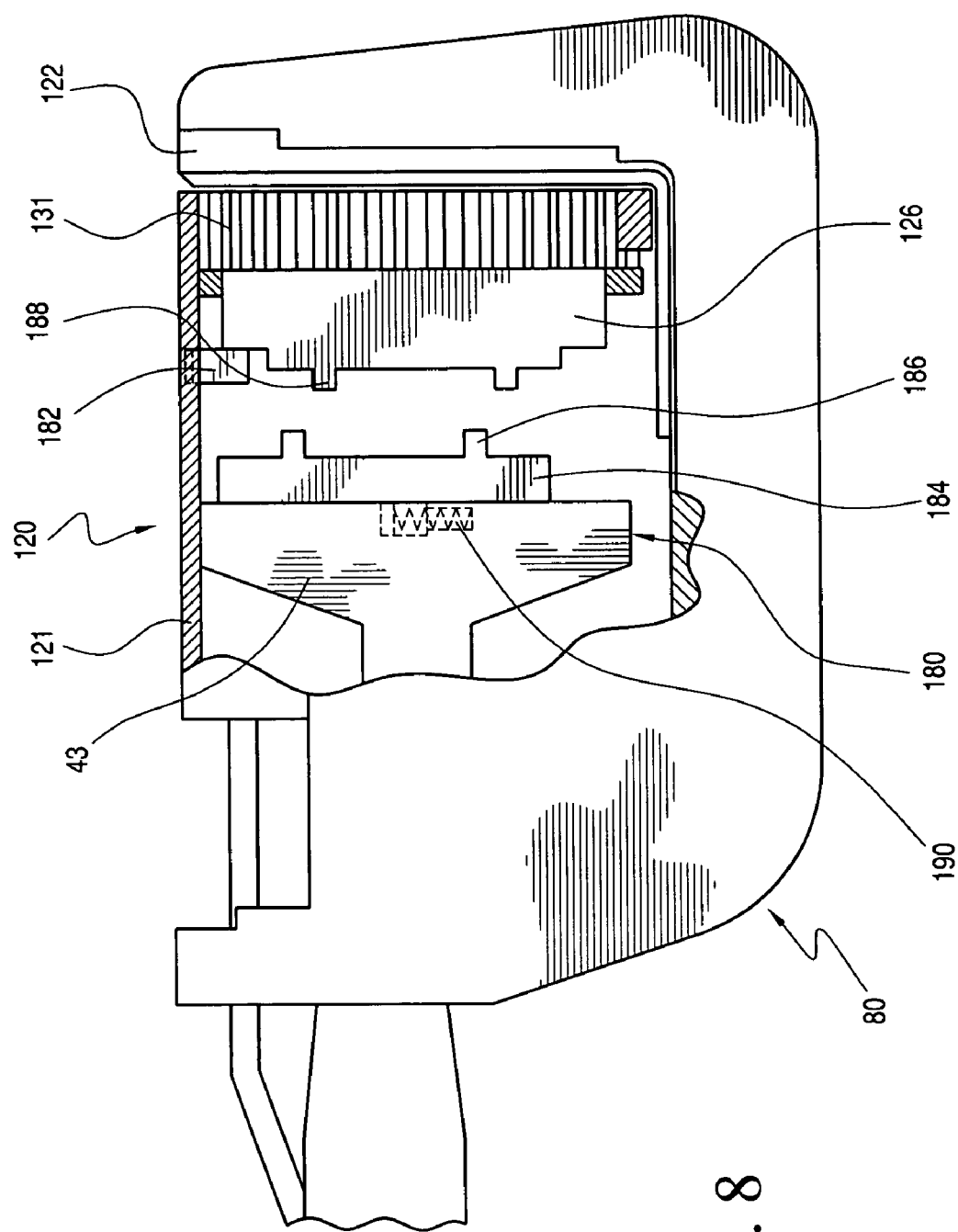

More particularly, and with reference to FIGS. 6 to 8, the lockout mechanism 180 includes a lock tab 182 integrally formed with the cartridge housing 121 of the cartridge module 120. The lockout mechanism 180 further includes a firing bar 43 having a slide bar 184 with forwardly extending tabs 186, or prongs, aligned with the knife 126 and driver 131 for subsequent contact therewith. The slide bar 184 is rotationally mounted to the distal end of the firing bar 43 and interacts with the lock tab 182 to control positioning thereof in a manner which will be discussed below in greater detail. As such, the lock tab 182 is shaped and dimensioned to engage the distal end of the firing bar 43, in particular, the side bar 184, both before and during actuation of the linear surgical stapler 20.

Prior to actuation of the firing transmission assembly, and with reference to FIG. 6, the lock tab 182 engages the slide bar 184 to ensure that the slide bar tabs 186 are properly aligned with knife tabs 188 extending rearwardly from the proximal end of the knife 126. Upon actuation of the firing transmission assembly and forward movement of the firing bar 43 (see FIG. 7), the distal end of the firing bar 43, which is provided with a forwardly extending slide bar 184 having aligned tabs 186 extending therefrom, contact the knife 126 and driver 131 to move the knife 126 and driver 131 forward into contact with the anvil 122 to form staples between the driver and anvil. Specifically, the slide bar 184 at the distal end of the firing bar 43 contacts knife tabs 188 rearwardly extending from the proximal end of the knife 126. It is the alignment of the slide bar tabs 186 with the knife tabs 188 that permits movement of the knife 126 to cut tissue in a desired manner. Movement of the knife 126 to this forward position ultimately results in cutting of the tissue.

In addition to moving the knife 126 and driver 131, the firing bar 43 also moves the lock tab 182 forward into alignment with the proximal side of the knife 126. As the firing bar 43 retracts (see FIG. 8), the cartridge housing 121 structure moves proximally, although the lock tab 182 remains substantially positioned adjacent the proximal end of the knife 126 and ceases to remain in contact with the slide bar 184. Without the lock tab 182 in contact with the slide bar 184, the slide bar 184 rotates to a lock position. In this lock position, the tabs 186 along the slide bar 184 are out of alignment with the knife tabs 188. In this position, although the firing bar 43 may still be moved distally toward the knife 126 and driver 131, the tabs 186 of the slide bar 184 will not contact the knife tabs 188 and the firing bar 43 is, therefore, unable to move the knife 126 forward toward the anvil 122.

As those skilled in the art will certainly appreciate, the present lockout mechanism may be employed in a variety of environments without departing from the spirit of the present invention. For example, the embodiment described above could be constructed solely as a stapler, without a knife and with the tabs formed on the driver.

Figure 9:
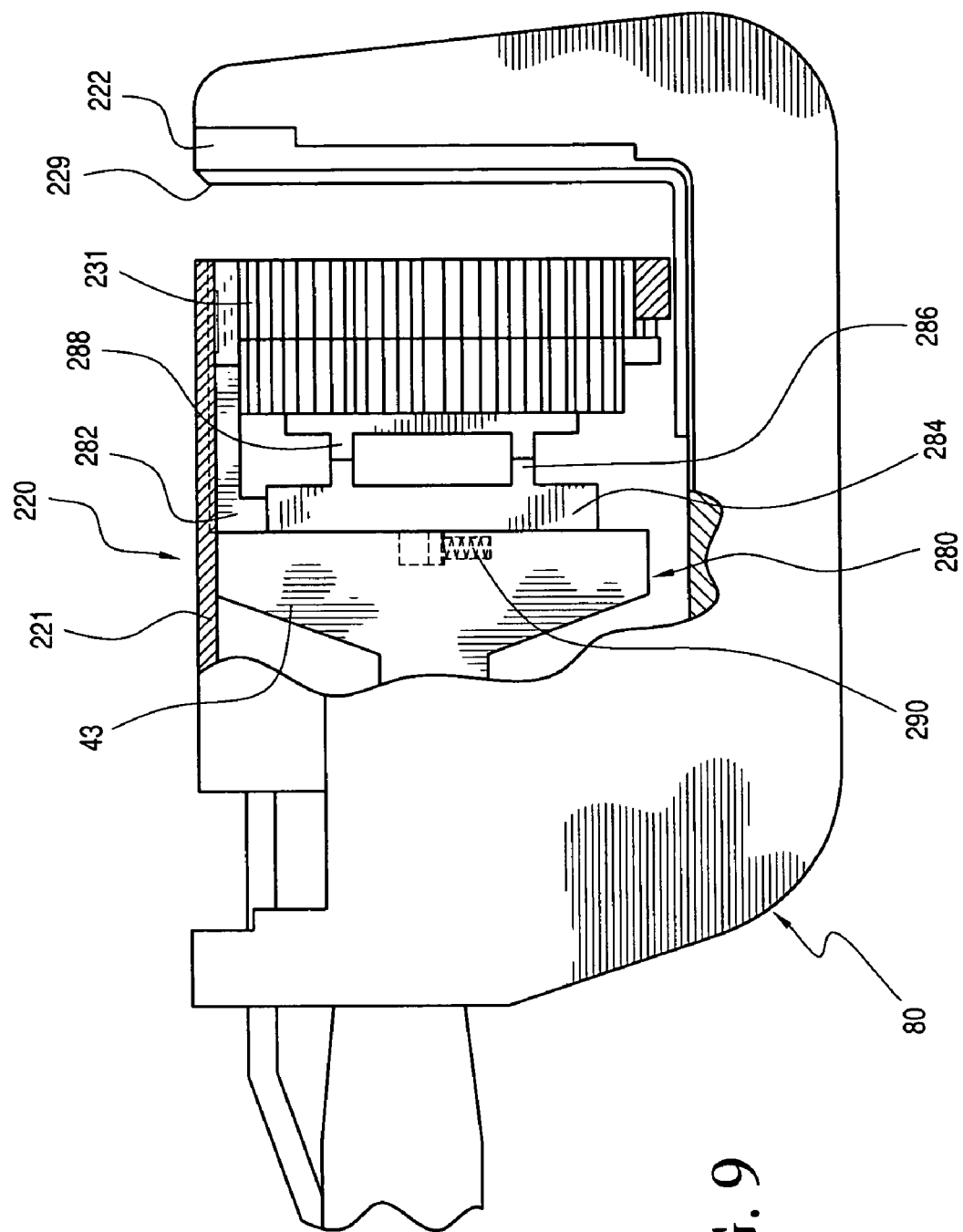
FIG. 9 through 11 show the various steps involved in the actuation of the present linear surgical stapler in accordance with an alternate embodiment thereof.
Figure 10:
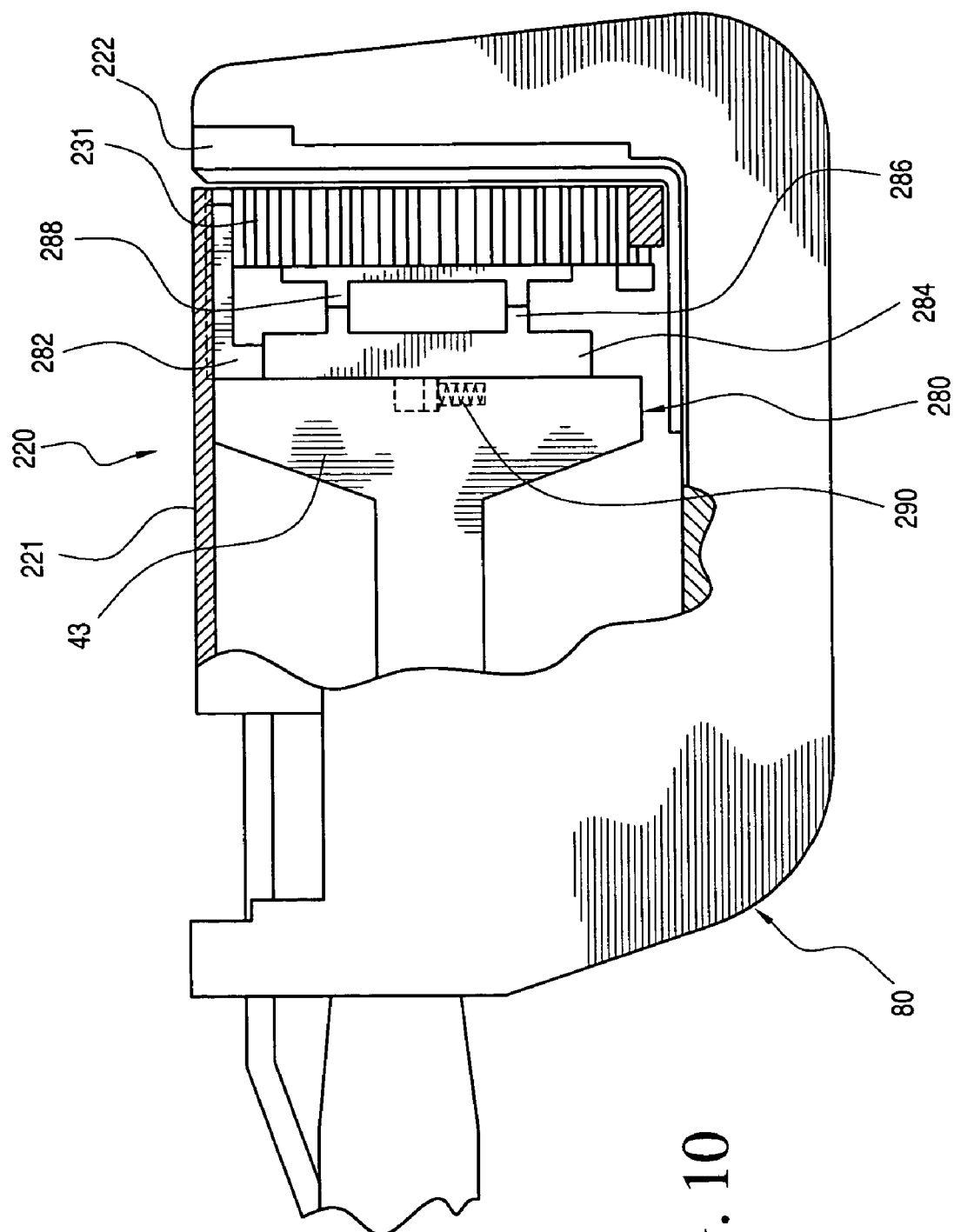
Figure 11:
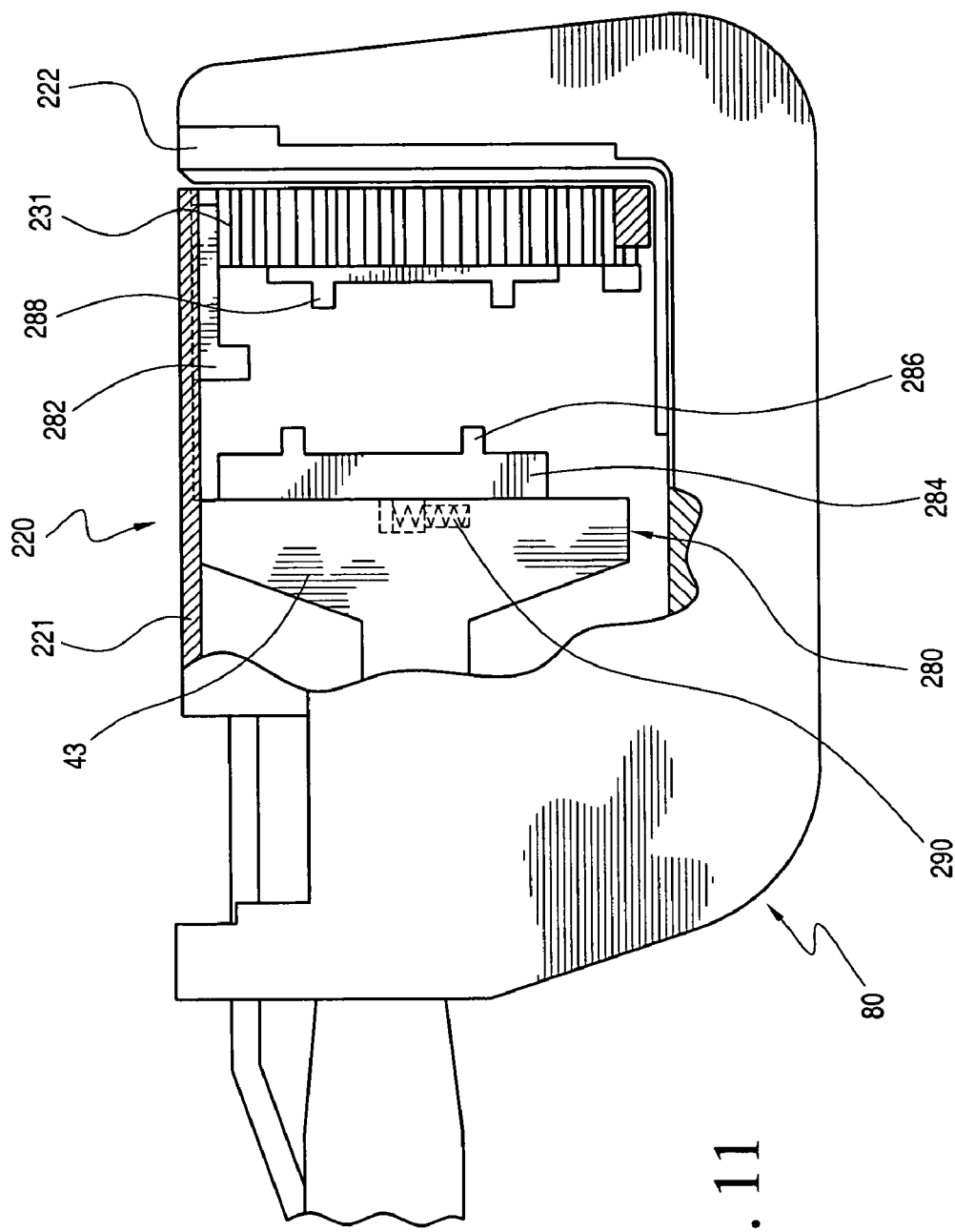

In addition, and with reference to FIGS. 9, 10 and 11, a variation of the present lockout mechanism may be employed in a surgical instrument not including a knife. In accordance with this embodiment, the knife is removed and the lock tab is formed as part of the driver and driver tabs. Although this embodiment discloses a variation of the lock tab structure disclosed above used in conjunction with an apparatus not including a knife, the various components of the two embodiments could certainly be interchanged without departing from the spirit of the invention.

With reference to FIGS. 9, 10 and 11, the components of this alternate embodiment of the fixed device lockout mechanism 280 will now be described. In accordance with a preferred embodiment of the present invention, the cartridge module 220 having a cartridge housing 221 is provided with a lock tab 282 that interferes with a slide bar 284 positioned at the distal end of the firing bar 43, moving the slide bar 284 so tabs 286 on the slide bar 284 are positioned in line with tabs 288 on the driver 231 prior to firing. In fact, the lock tab 282 is formed as part of the driver 231 and moves with the driver 231 during approximation and firing.

When the firing transmission assembly is moved distally, the firing bar 43 moves the driver 231 toward the tissue, thus stapling the predetermined tissue area. During approximation and firing, the lock tab 282 is moved distally with the driver 231 to a neutral position in the cartridge module 220. After the firing transmission assembly is retracted, the driver 231 and the lock tab 282 remain in the distal position in the cartridge module 220. The slide bar 284 then moves into its disconnect position by a spring 290 because the lock tab 282 no longer forces it into its firing position.

The firing bar 43 is free to move distally thereafter as it will not engage or actuate the driver 231. More particularly, the driver 231 will not move with the firing bar 43 because the tabs 286 of the slide bar 284 move into a disconnect position out of alignment with the tabs 288 of the driver 231. The driver 231 remains in the forward proximal position apart from the firing bar 43 after firing.

More particularly, and with reference to FIGS. 9 to 11, the lockout mechanism 280 includes a lock tab 282 integrally formed with the driver 231. The lockout mechanism 280 further includes a firing bar 43 having a slide bar 284 with forwardly extending tabs 286, or prongs, aligned with the driver 231 for subsequent contact therewith. The slide bar 284 is mounted to the distal end of the firing bar 43 in a manner permitting movement relative thereto and interacts with the lock tab 282 to control positioning thereof in a manner which will be discussed below in greater detail. The lock tab 282 is shaped and dimensioned to engage the distal end of the firing bar 43, in particular, the side bar 284, both before and during actuation of the linear surgical stapler 20.

Prior to actuation of the firing transmission assembly, and with reference to FIG. 9, the lock tab 282 engages the slide bar 284 to ensure that the slide bar tabs 286 are properly aligned with driver tabs 288 extending rearwardly from the proximal end of the driver 231. Upon actuation of the firing transmission assembly and forward movement of the firing bar 43 (see FIG. 10), the distal end of the firing bar 43, which is provided with a forwardly extending slide bar 284 having aligned tabs 286 extending therefrom, contacts the driver 231 to move the driver 231 forward into contact with the anvil 222 to form staples between the driver 231 and anvil 222. Specifically, the slide bar 284 at the distal end of the firing bar 43 contacts driver tabs 288 rearwardly extending from the proximal end of the driver 231. It is the alignment of the slide bar tabs 286 with the knife tabs 288 that permits movement of the driver 231 to fire the staples in a desired manner.

In addition to moving the driver 231, the firing bar 43 also moves the lock tab 282 forward with the driver 231 to which it is attached. As the firing bar 43 retracts (see FIG. 11), the lock tab 282 remains substantially positioned adjacent the proximal end of the driver 231 and ceases to remain in contact with the slide bar 284. Without the lock tab 282 in contact with the slide bar 284, the slide bar 284 moves to a lock position. In this lock position, the tabs 286 along the slide bar 284 are out of alignment with the driver tabs 288. In this position, although the firing bar 43 may still be moved distally toward the driver 231, the tabs 286 of the slide bar 284 will not contact the driver tabs 288 and the firing bar 43 is, therefore, unable to move the driver 231 forward toward the anvil 222.

As those skilled in the art may appreciate, it is possible the firing bar could contact the lock tab attached to the driver and slightly push the driver forward even after the slide bar has moved. However, this may be remedied in a variety of ways by moving the lock tab out of alignment with the firing bar after actuation thereof or otherwise preventing the firing bar from engaging the lock tab after actuation thereof. For example, the device could be made such that the firing bar no longer lies transversely relative to the lock tab after firing.

The present invention overcomes the deficiency of the prior art in that prior art designs mechanically prevent the firing bar from moving distally. As such, and unlike prior art lockout systems which require the device to survive high stress if the user should try to defeat the lockout mechanism, the present lockout mechanism disengages the firing mechanism altogether removing any force transmission that would require the device to survive high loads, that is, the firing bar is entirely disconnected from the driver and/or knife after firing thereof. This allows for a wider range of materials that could be used to produce the device and structures that are less bulky as the device does not have to survive high lockout loads. This would allow for easier manufacturability and cost savings while giving the user a more ergonomically compatible device. In addition, the present lockout mechanism provides clear feedback that the lockout mechanism has been activated and may, therefore, not be confused with a jammed system; that is, after the system is fired the firing bar moves freely in a manner which is clearly indicative of a fired system and could not be confused with a jammed system.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A surgical stapler adapted for applying a plurality of surgical fasteners to body tissue, the surgical stapler comprising:
    an anvil structure;
    a cartridge housing including at least one component for the application of surgical fasteners housed therein;
    a firing mechanism including a firing bar having a distal end and a slide bar mounted on the distal end of the firing bar for movement relative to the firing bar; and
    a lockout mechanism for activation and deactivation of the firing mechanism by disconnecting the distal end of the firing bar from the component housed within the cartridge housing.

2. The surgical stapler according to claim 1, wherein the cartridge housing contains a plurality of surgical fasteners and a knife, the cartridge housing and anvil structure being relatively movable between a first spaced apart position and a second position in close approximation with one another.

3. The surgical stapler according to claim 2, wherein the firing mechanism is associated with the cartridge housing for ejecting the surgical fasteners from the cartridge housing to be driven against the anvil structure.

4. The surgical stapler according to claim 3, wherein the lockout mechanism includes a lock tab that interferes with the slide bar of the firing mechanism moving the slide bar such that tabs on the slide bar move out of alignment with tabs on the knife during firing of the surgical stapler to disconnect the firing mechanism from the knife and prevent subsequent firing of the surgical stapler.

5. The surgical stapler according to claim 4, wherein after the lock tab is moved distally the firing mechanism is retracted, and the lock tab remains in the distal position in the cartridge housing.

6. The surgical stapler according to claim 5, wherein retraction of the firing mechanism causes the slide bar to be moved away from the lock tab, and the slide bar moves into its disconnect position.

7. The surgical stapler according to claim 1, wherein the cartridge housing contains a plurality of surgical fasteners and a driver, the cartridge housing and anvil structure being relatively movable between a first spaced apart position and a second position in close approximation with one another.

8. The surgical stapler according to claim 7, wherein the firing mechanism is associated with the cartridge housing for ejecting the surgical fasteners from the cartridge housing to be driven against the anvil structure.

9. The surgical stapler according to claim 8, wherein the lockout mechanism includes a lock tab that interferes with the slide bar of the firing mechanism moving the slide bar such that tabs on the slide bar move out of alignment with tabs on the driver during firing of the surgical stapler to disconnect the firing mechanism from the driver and prevent subsequent firing of the surgical stapler.

10. The surgical stapler according to claim 9, wherein after the lock tab is moved distally the firing mechanism is retracted, and the lock tab remains in the distal position in the cartridge housing.

11. The surgical stapler according to claim 10, wherein retraction of the firing mechanism causes the slide bar to be moved away from the lock tab, and the slide bar moves into its disconnect position.

12. The surgical stapler according to claim 1, wherein slide bar is spring biased.

13. The surgical stapler according to claim 1, wherein prior to actuation of the firing mechanism the slide bar includes distally extending prongs aligned with the component housed within the cartridge housing of the surgical stapler for subsequent contact therewith.

14. The surgical stapler according to claim 13, wherein prior to actuation of the firing mechanism a lock tab engages the slide bar to ensure that the prongs are properly aligned with proximally extending tabs formed along the component housed within the cartridge housing.

15. A lockout mechanism that interacts with a cartridge housing of a surgical stapler for selective activation and deactivation thereof, the surgical stapler includes an anvil structure and a cartridge housing, the surgical stapler also includes a firing mechanism associated with the cartridge housing for ejecting surgical fasteners from the cartridge housing to be driven against the anvil structure, the firing mechanism including a firing bar having a distal end which is adjacent the cartridge housing, and a slide bar mounted on the distal end of the firing bar for movement relative to the firing bar, the lockout mechanism comprising:
    a lock tab that interferes with the slide bar of the firing mechanism moving the slide bar such that tabs on the slide bar move out of alignment with tabs on a component housed within the cartridge housing during firing of the surgical stapler to prevent subsequent firing of the linear surgical stapler.

16. The lockout mechanism according to claim 15, wherein during firing of the surgical stapler the firing mechanism moves the lock tab distally to a neutral position in the cartridge housing.

17. The lockout mechanism according to claim 16, wherein after the lock tab is moved distally the firing mechanism is retracted, and the lock tab remains in the distal position in the cartridge housing.

18. The lockout mechanism according to claim 17, wherein retraction of the firing mechanism causes the slide bar to be moved away from the lock tab, and the slide bar moves into its disconnect position.

19. The lockout mechanism according to claim 15, wherein the slide bar is spring biased.

20. The lockout mechanism according to claim 15, wherein prior to actuation of the firing mechanism the slide bar includes distally extending prongs aligned with the components of the cartridge housing for subsequent contact therewith.

* * * * *